United States Patent [19]

Knaup et al.

[11] Patent Number: 5,103,048

[45] Date of Patent: Apr. 7, 1992

[54] SURFACE-ACTIVE COMPOUNDS HAVING A PERFLUOROALKYL GROUP AND A NITROGEN-CONTAINING ALIPHATIC RADICAL, A PROCESS FOR THEIR PREPARATION AND THEIR USE

[75] Inventors: Wolfgang Knaup, Burgkirchen; Frank Wehowsky, Niedernhausen; Norbert Schmitt, Burgkirchen, all of Fed. Rep. of Germany

[73] Assignee: Hoechst Aktiengesellschaft, Frankfurt am Main, Fed. Rep. of Germany

[21] Appl. No.: 634,023

[22] Filed: Dec. 26, 1990

[30] Foreign Application Priority Data

Dec. 28, 1989 [DE] Fed. Rep. of Germany ....... 3943128

[51] Int. Cl.$^5$ .......................................... C07C 227/24
[52] U.S. Cl. ................................. 562/568; 562/567; 562/107; 564/504; 564/505; 560/170
[58] Field of Search ................. 562/568, 567; 560/170; 564/504, 505

[56] References Cited

U.S. PATENT DOCUMENTS 3,836,552  9/1974  Stach et al. .
4,165,338  8/1979  Katsushima et al. ............... 560/170

FOREIGN PATENT DOCUMENTS 3724198  2/1989  Fed. Rep. of Germany .

Primary Examiner—Jose G. Dees
Assistant Examiner—Keith MacMillan

[57] ABSTRACT

The new compounds have the formula below

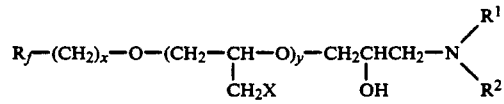

in which
$R_f$ is a perfluoroalkyl radical having 4 to 20 carbon atoms,
x is 1 to 4,
y is 1 to 10,
X is Br, Cl or I, and
$R^1$ and $R^2$ are hydrogen or a $C_1$ to $C_4$-alkyl radical or a water-solubilizing aliphatic radical, with the proviso that at least one of the two substituents $R^1$ and $R^2$ is a water-solubilizing aliphatic radical.

The surface-active compounds described are prepared by reacting a suitable epoxide with a suitable amine. They are used in particular for the preparation of foaming agents.

2 Claims, No Drawings

SURFACE-ACTIVE COMPOUNDS HAVING A PERFLUOROALKYL GROUP AND A NITROGEN-CONTAINING ALIPHATIC RADICAL, A PROCESS FOR THEIR PREPARATION AND THEIR USE

DESCRIPTION

The invention relates to surface-active compounds having a perfluoroalkyl group and a nitrogen-containing aliphatic radical, to a process for the preparation of these compounds and to their use.

For certain purposes, for example for preparing foaming agents, chemical compounds are required which have the effect of substantially lowering the surface tension of water or of aqueous systems and additionally have a strong foaming effect. The prior art has shown that compounds having a perfluoroalkyl group and a nitrogen-containing aliphatic radical in the molecule have at least one of the two properties.

Thus, U.S. Pat. No. 3,836,522 describes surface-active perfluoroalkylamidoamine compounds. Compared with analogous fluoro surfactants, they have better water solubility and lower the surface tension of aqueous systems to a larger extent when the same amount is used. However, as regards foaming, they leave something to be desired. German Offenlegungsschrift DE 3,724,198 A1, in which perfluoroalkyl- and epihalogenohydrin-containing epoxides are described, should also be mentioned here. The epoxides described have the formula

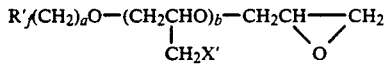

in which
R'$_f$ is a perfluoroalkyl radical having 4 to 20 carbon atoms, preferably 6 to 16 carbon atoms,
a is 1 to 4, preferably 2,
b is 1 to 20, preferably 1 to 10, and
X, is Br, Cl or I, preferably Br or Cl.

With respect to the properties of these epoxides, they are said to be easily polymerizable and therefore constitute an advantageous monomer for preparing fluorine-containing epoxy resins and furthermore are said to have high compatibility with non-fluorinated epoxides and to give textiles and leather good oleophobicity and hydrophobicity.

Starting from the prior art, according to which compounds having a perfluoroalkyl group and a nitrogen-containing aliphatic radical have advantageous surface-active properties, the object of the invention is to find further efficient compounds of this type. The new compounds should have good water solubility and have the effect of significantly lowering the surface tension of water or aqueous systems even by a small amount. Moreover, they should also have high foaming capacity. This means that not only lowering of the surface tension in water or aqueous systems but also foam formation should be achieved by means of the new compounds.

The surface-active compounds according to the invention have the formula 1 below

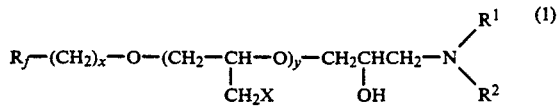

in which
R$_f$ is a perfluoroalkyl radical having 4 to 20 carbon atoms, preferably 6 to 16 carbon atoms,
x is 1 to 4, preferably 2,
y is 1 to 10, preferably 1 to 5,
X is Br, Cl or I, preferably Cl, and
R$^1$ and R$^2$ are hydrogen or a C$_1$ to C$_4$-alkyl radical or a water-solubilizing aliphatic radical, with the proviso that at least one of the two substituents R$^1$ and R$^2$ is a water-solubilizing aliphatic radical.

The invention is based on the surprising finding that the combination of the perfluoroalkyl- and epihalogenohydrin-containing epoxides described in the German Offenlegungsschrift DE 3,724,198 A1 mentioned, i.e. epoxides of the formula 2 below

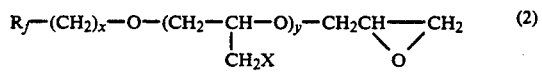

in which R$_f$, x, y and X have the meanings mentioned with certain aliphatic amine compounds gives products which achieve the object to a particularly high degree.

The perfluoroalkyl group R$_f$ can be straight-chain or branched, saturated or unsaturated (preferably having 1 to 3 double bonds), saturated being preferred. In the case of a branched perfluoroalkyl group, the terminal-branched group is preferred. The perfluoroalkyl radical is frequently a mixture of perfluoroalkyl having the numbers of carbon atoms mentioned, i.e. 4 to 20 carbon atoms, preferably 6 to 16 carbon atoms.

R$^1$ and R$^2$ are a water-solubilizing aliphatic radical or a C$_1$ to C$_4$-alkyl radical or a hydrogen atom, although only R$^1$ or only R$^2$ is a C$_1$ to C$_4$-alkyl radical or H. This means that at least one water-solubilizing aliphatic radical should be present on the nitrogen atom of the formula 1. As regards the water-solubilizing aliphatic radical, R$^1$ and R$^2$ can be identical or different, and are preferably identical. The water-solubilizing radicals are preferably those from the group comprising hydroxyalkylene radicals, alkylenecarboxylate radicals, alkylenesulfonate radicals and radicals of the formula

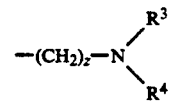

in which z is 1 to 10, preferably 1 to 5, and R$^3$ and R$^4$ have the meanings of R$^1$ and R$^2$. Particularly preferred water-solubilizing aliphatic radicals are those from the group comprising hydroxyalkylene radicals of the formula —(CH$_2$)$_m$—OH, alkylenecarboxylate radicals of the formula —(CH$_2$)$_n$—COOM, alkylenesulfonate radicals of the formula —(CH$_2$)$_w$—SO$_3$M and radicals of the formula

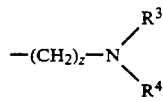

in which $R^3$ and $R^4$ have the meanings of $R^1$ and $R^2$, and are each preferably —CH$_2$CH$_2$OH, and, m, n, w and z are 1 to 10, preferably 1 to 5, and M is H or preferably a cation. The cation is preferably an alkali metal cation or an ammonium or organoammonium cation.

Below, a few exemplary compounds of the formula 1 are mentioned, the expression

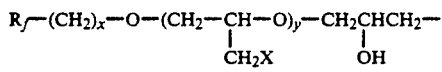

in formula 1 being set equal to A and M having the meanings mentioned:

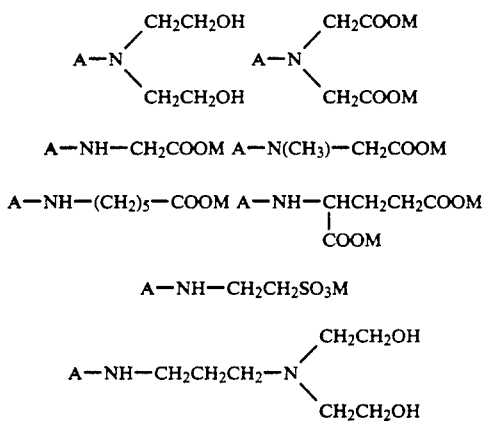

The preparation of the compounds according to the invention is evident from the formula 1. According to a preferred process, their preparation is carried out by reacting the abovementioned epoxides of the formula 2

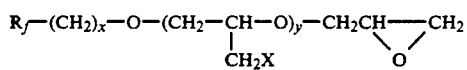 (2)

with an aliphatic amine of the formula 3 below

 (3)

in which $R^1$ and $R^2$ have the meanings mentioned, in a molar ratio of 1:1.

The epoxides of the formula 2 and their preparation are described in detail in the German Offenlegungsschrift DE 3,724,198 A1 mentioned, herein incorporated by reference. They are liquid to wax-like solid, yellow to brown-colored products. They are obtained by reacting a fluoro alcohol/epihalogenohydrin adduct of the formula below

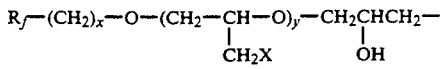

in which $R_f$, x, y and X have the meanings mentioned, to eliminate hydrogen halide with cyclization of the halogenohydrin group of the adduct with alkali metal hydroxides or alkaline earth metal hydroxides in the form of an aqueous solution, in the presence of phase transfer catalysts and at a pH of 9 to 12, and isolating the desired epoxide compound formed from the reaction mixture. The aliphatic amines of the formula 3 mentioned are also part of the prior art. They are, as is quite obvious, well-known products.

The preparation of the surface-active compounds according to the invention is carried out by reacting an epoxide of the formula 2 with an aliphatic amine of the formula 3 in a molar ratio of 1:1. The reaction temperature is 40° to 120° C., preferably 50° to 100° C. The reaction can be carried out in the melt, i.e. without solvent, or by using a solvent. Preferred solvents are the C$_1$ to C$_4$-alkanols. The reaction between the amine compound and the epoxide proceeds quantitatively. If the reaction is not carried out without a solvent, the desired compound can be isolated, (if it is not desired in solution in the first place), for example, by separating off the solvent and any water present by distillation. The compounds according to the invention are liquid to waxlike, white to brown-colored products at room temperature.

The compounds according to the invention have a series of advantages. They have good water solubility and have the effect not only of substantially lowering the surface tension in water or aqueous systems even by a small amount but also have a strong foaming effect. Due to this combination of properties, they can be used in many applications, in particular as foaming agents. This is especially true of those compounds according to the invention containing the alkylenecarboxylate radicals mentioned as water-solubilizing group. The preparation of a foaming agent by means of the compounds according to the invention is carried out by known methods. An aqueous solution containing at least one compound according to the invention in an efficient amount is prepared, i.e. in such an amount that the solution produces the desired amount of foam upon stirring, shaking or spraying by means of air or another blowing agent. This amount, expressed in grams per liter of water, is 0.1 to 10 g/l, preferably 0.5 to 5 g/l, which corresponds to 0.01 to 1% by weight, preferably 0.05 to 0.5% by weight, the weight percentage being based on the weight of the aqueous solution. The compounds according to the invention can be combined with conventional foaming aids, for example with protein products, such as keratins, albumins, globulins, ground seeds and the like, unmodified or modified by hydrolysis and stabilized with salts of polyvalent metals. An area of application for foaming agents containing the compounds according to the invention is the extinction of fires caused by liquid hydrocarbons, such as car gasoline, airplane fuel and the like. As is known, this is done by spraying the foaming agent, as a result of which a thick foam cover extends over the entire burning area.

The invention is now illustrated in more detail by way of examples.

EXAMPLE 1

68.4 g (0.651 mol) of the amine of the formula $$HN\begin{array}{c}CH_2CH_2OH\\ \\CH_2CH_2OH\end{array}$$

i.e. diethanolamine, were initially introduced into a reaction vessel equipped with a stirrer. The initially introduced product was heated to 60° C., and 360.0 g (0.651 mol) of the epoxide of the formula $$C_6F_{13}-CH_2CH_2O-CH_2-\underset{\underset{CH_2Cl}{|}}{CH}-O-CH_2\underset{\underset{O}{\diagdown\diagup}}{CH-CH_2}$$

were added at this temperature in the course of one hour. After the addition of the amount of epoxide, the mixture was kept at 60° C. (while stirring) for another 6 hours. After this time, the amine and the epoxide had reacted completely to give the compound according to the invention of the formula $$C_6F_{13}CH_2CH_2O-CH_2-\underset{\underset{CH_2Cl}{|}}{CH}-O-CH_2\underset{\underset{OH}{|}}{CH}-CH_2-N\begin{array}{c}CH_2CH_2OH\\ \\CH_2CH_2OH\end{array}$$

A more or less wax-like, yellow-colored product was present at room temperature.

EXAMPLE 2

18.2 g (0.136 mol) of iminodiacetic acid, 19.8 g of isopropanol and 10.9 g (0.272 mol) of NaOH in the form of an 18% strength by weight aqueous solution were initially introduced into a reaction vessel equipped with a stirrer. The mixture was heated to 60° C., and 70.0 g (0.136 mol) of the epoxide of the formula $$C_{10}F_{21}-CH_2CH_2O-CH_2-\underset{\underset{CH_2Cl}{|}}{CH}-O-CH_2\underset{\underset{O}{\diagdown\diagup}}{CH-CH_2}$$

were added at this temperature in the course of 4 hours. After the addition of the amount of epoxide, the mixture was maintained at 65° C. for another 4 hours. After this time, the amine compound and the epoxide had reacted completely to give the compound according to the invention of the formula $$C_{10}F_{21}-CH_2CH_2O-CH_2-\underset{\underset{CH_2Cl}{|}}{CH}-O-CH_2\underset{\underset{OH}{|}}{CH}-CH_2-N\begin{array}{c}CH_2COONa\\ \\CH_2COONa\end{array}$$

The compound according to the invention, a wax-like, yellow-colored product, was present in the form of a dispersion in the solvent mentioned (the perfluoroalkyl radical $C_{10}F_{21}$ represents the perfluoroalkyl mixture $C_8F_{17}$ to $C_{16}F_{33}$).

EXAMPLE 3

21.6 g (0.165 mol) of ε-aminocapronic acid, 100 g of methanol and 6.6 g (0.165 mol) of NaOH in the form of a 40% strength by weight aqueous solution were initially introduced into a reaction vessel equipped with a stirrer. The mixture was heated to 65° C., and 91.0 g (0.165 mol) of the epoxide from Example 1 were added at this temperature in the course of one hour. After the addition of the amount of epoxide, the mixture was maintained at 65° C. for another 6 hours. After this time, the amine compound and the epoxide had completely reacted to give the compound according to the invention of the formula $$C_6F_{13}-CH_2CH_2O-CH_2-\underset{\underset{CH_2Cl}{|}}{CH}-O-CH_2\underset{\underset{OH}{|}}{CH}-CH_2-\underset{\underset{H}{|}}{N}-(CH_2)_5-COONa$$

After the water present and the methanol had been separated off by distillation, the compound according to the invention was present in the form of a wax-like, yellow-colored product.

EXAMPLE 4

Amounts used:
27.8 g (0.189 mol) of glutamic acid
200 ml of methanol
15.1 g (0.378 mol) of NaOH in the form of a 40% strength by weight aqueous solution
100.0 g (0.189 mol) of the epoxide from Example 1.

Procedure: as in Example 3.

The compound according to the invention, a wax-like, yellow-colored product, has the formula below $$C_6F_{13}-CH_2CH_2O-CH_2-\underset{\underset{CH_2Cl}{|}}{CH}-O-CH_2\underset{\underset{OH}{|}}{CH}-CH_2-\underset{\underset{H}{|}}{N}-\underset{\underset{COONa}{|}}{CH}CH_2CH_2COONa$$

EXAMPLE 5

Amounts used:
77.9 g (0.48 mol) of the amine compound of the formula $$H_2N-CH_2CH_2CH_2N\begin{array}{c}CH_2CH_2OH\\ \\CH_2CH_2OH\end{array}$$

301.9 g (0.48 mol) of the epoxide from Example 2.
Procedure: as in Example 1.
The compound according to the invention, a wax-like, yellow-colored product, has the formula below

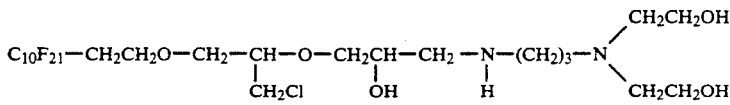

Example 2 was repeated, except that 107.2 g (0.136 mol) of the epoxide of the formula

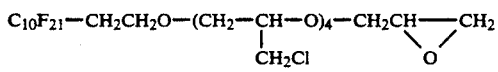

were added in the course of 4 hours. The compound according to the invention obtained corresponds to that of Example with respect to appearance and has an analogous formula.

The compounds according to the invention of Examples 1 to and a compound of the prior art, i.e. the compound of Example 1 of the U.S. Pat. No. 3,836,552 mentioned at the beginning, of the formula

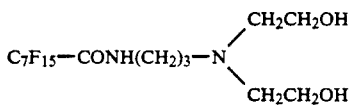

was tested with respect to lowering of the surface tension and foam formation.

The surface tension was determined by DIN 53 914. 0.1 g and 1 g of each compound were dissolved in one liter each of fully deionized water. The surface tension of these solutions was measured at 20° C. with a conventional tensiometer by the ring detachment method in mN/m.

The foaming was determined by DIN 59 902. 0.5 g and 2 g of each compound were dissolved in one liter each of fully deionized water. Of these solutions, 200 ml were transferred to a 1000 ml graduated cylinder and beaten at 25° C. thirty times with a perforated disk. The resulting foam height in the graduated cylinder, expressed in milliliters, represents the foam value.

The results are summarized in the table below.

The compounds according to the invention have a significantly higher foam value, i.e. a substantially higher foaming capacity, than the compounds of the prior art. With respect to the lowering of the surface tension, the compound of the prior art has a good value, however, the values of the compounds according to the invention are still good, especially since the surface tension of the water (75 mN/m at 20° C.) is lowered by more than 70%. With respect to the combination of the two properties, i.e. the lowering of the surface tension and foaming, the compounds according to the invention are thus superior to the prior art to an unexpected extent.

TABLE

| Compounds of Examples 1 to 6 | Surface tension (mN/m) | | Foam value (ml) | |
|---|---|---|---|---|
| | 0.1 g/l | 1 g/l | 0.5 g/l | 2 g/l |
| 1 | 21 | 18 | 70 | 150 |
| 2 | 23 | 17 | 500 | 670 |
| 3 | 24 | 20 | 260 | 570 |
| 4 | 23 | 19 | 380 | 660 |
| 5 | 25 | 26 | 100 | 270 |
| 6 | 25 | 22 | 480 | 640 |
| Comparative compound | 21 | 18 | 50 | 100 |

We claim:

1. A surface-active compound having a perfluoroalkyl group and a nitrogen-containing aliphatic radical, of the formula

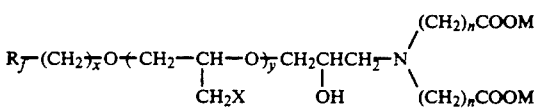

in which $R_f$ is a perfluoroalkyl radical having 6 to 16 carbon atoms, x is 2, y is 1 to 5, x is Cl, n is 1 to 5, and M is H or an alkali metal.

2. A surface-active compound having a perfluoroalkyl group and a nitrogen-containing aliphatic radical, of the formula

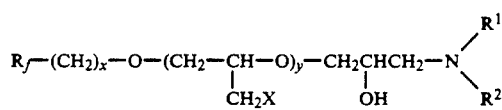

in which $R_f$ is a perfluoroalkyl radical having 6 to 16 carbon atoms, x is 2, y is 1 to 5, x is Cl, and $R^1$ and $R^2$ are a water-solubilizing aliphatic radical selected from the group consisting of hydroxyalkylene radicals of the formula —$(CH_2)_m$—OH and alkylene-carboxylate radicals of the formula —$(CH_2)_n$—COOM in which m and n are 1 to 5 and M is H or an alkali metal.

* * * * *